US007189520B2

(12) United States Patent
Muldoon et al.

(10) Patent No.: US 7,189,520 B2
(45) Date of Patent: Mar. 13, 2007

(54) COMPOSITIONS AND METHODS FOR DETECTING ANIMAL BYPRODUCT IN FEED

(75) Inventors: Mark T. Muldoon, Elkton, MD (US); Dale V. Onisk, Bear, DE (US); Michael C. Brown, North East, MD (US); Christina Straughen, Pennsville, NJ (US); James W. Stave, Bear, DE (US)

(73) Assignee: Strategic Diagnostics Inc., Newark, DE (US)

( * ) Notice: Subject to any disclaimer, the term of this patent is extended or adjusted under 35 U.S.C. 154(b) by 0 days.

(21) Appl. No.: 10/734,654

(22) Filed: Dec. 12, 2003

(65) Prior Publication Data

US 2004/0166537 A1 Aug. 26, 2004

Related U.S. Application Data

(60) Provisional application No. 60/450,765, filed on Feb. 27, 2003, provisional application No. 60/432,924, filed on Dec. 12, 2002.

(51) Int. Cl.
*G01N 33/53* (2006.01)

(52) U.S. Cl. ............... 435/7.1; 435/7.92; 435/7.93; 435/7.94; 436/518

(58) Field of Classification Search ............... 435/7.1, 435/7.92–7.94, 7.95, 810, 975; 436/518, 436/524, 63
See application file for complete search history.

(56) References Cited

U.S. PATENT DOCUMENTS

| 3,654,090 | A | * | 4/1972 | Schuurs et al. | ............ 435/7.93 |
| 4,444,879 | A | * | 4/1984 | Foster et al. | ............... 435/7.95 |
| 5,437,981 | A | * | 8/1995 | Deger et al. | .................. 435/7.1 |
| 5,571,682 | A | * | 11/1996 | Jacobs et al. | ................ 435/7.9 |
| 5,910,446 | A | * | 6/1999 | Ansfield | ..................... 436/21 |
| 6,022,694 | A | * | 2/2000 | Radziejewski et al. | ...... 435/7.1 |
| 6,150,172 | A | * | 11/2000 | Schmerr et al. | ............ 530/350 |
| 6,165,784 | A | | 12/2000 | O'Rourke et al. | |
| 6,214,565 | B1 | | 4/2001 | Prusiner et al. | |
| 6,617,116 | B2 | * | 9/2003 | Guan et al. | .................. 435/7.1 |
| 2003/0022248 | A1 | * | 1/2003 | Hsieh et al. | ............... 435/7.21 |
| 2003/0083255 | A1 | * | 5/2003 | Thorn et al. | .................. 514/12 |
| 2004/0043107 | A1 | * | 3/2004 | Ligt et al. | ...................... 426/2 |

OTHER PUBLICATIONS

Ansfield, Production of a Sensitive Immunoassay for Detection of ruminant Proteins in Rendered animal Material Heated to > 130 degrees C, Food & Agricultural Immunology (1994) 6, 419-433.*
Hamilton, Real and Perceived Issues Animal Proteins, FAO presentation, Bangkok, Apr. 29-May 3, 2002, pp. 1-16.*
Chen et al., Monoclonal antibodies against troponin I for the detection of rendered muscle tissues in animal feedstuffs, Meat Science (2002), 62 (4), 405-412.*
Voller, Diagnostic Horizons, Published by Microbiological Associates, Walkersville, Maryland 21793, The Enzyme Linked Immunosorbent Assay, vol. 2, No. 1, Feb. 1978, pp. 1-7.*
John F. Kearney et al.; *A New Mouse Myeloma Cell Line That Has Lost Immunoglobulin Expression but Permits the Construction of Antibody-Secreting Hybrid Cell Lines*; The Journal of Immunology; vol. 123, No. 4, Oct. 1979; pp. 1548-1550.
Ferrucio Santoro et al; *Activation of Complement by Schistosoma Mansori Schistosomula: Killing of Parasited by the Alternative Pathway and Requirement of IgG for Classical Pathway Activation;* The Journal of Immunology; vol. 123, No. 4, Oct. 1979; pp. 1551-1557.

* cited by examiner

*Primary Examiner*—Long V. Le
*Assistant Examiner*—Gary W. Counts
(74) *Attorney, Agent, or Firm*—Kilpatrick Stockton LLP

(57) ABSTRACT

Analytes and ligands for detecting animal byproduct in agricultural samples such as animal feed to minimize the transmission of prion pathogens into food products consumed by humans. The analyte is a component of rendered animal byproduct such as meat and bone meal (MBM). An antibody specific for the analyte is produced by immunizing an animal with MBM or an immunogenic component of MBM that is found in rendered animal product.

7 Claims, 8 Drawing Sheets

COMPOSITIONS AND METHODS FOR DETECTING ANIMAL BYPRODUCT IN FEED

CROSS-REFERENCE TO RELATED APPLICATIONS

This application claims priority to U.S. Provisional Application No. 60/432,924 filed Dec. 12, 2002 and U.S. Provisional Application No. 60/450,765 filed Feb. 27, 2003, both of which are incorporated herein by reference.

FIELD OF THE INVENTION

The present invention relates to the field of microbiology and more specifically relates to compositions and methods for the detection of rendered animal byproducts in animal feed.

BACKGROUND OF THE INVENTION

Transmissible spongiform encephalopathies are believed to be caused by infection with prion pathogens. Prions have some properties in common with other infectious pathogens, but do not appear to contain nucleic acid. Prion proteins accumulate in the central nervous system where they cause neuropathologic changes and neurological dysfunction. Specific examples of transmissible spongiform encephalopathies include but are not limited to scrapie, which affects sheep and goats; bovine spongiform encephalopathy (BSE), which affects cattle; feline spongiform encephalopathy and chronic wasting disease of deer and elk. In humans examples of transmissible spongiform encephalopathies include but are not limited to kuru, Creutzfeldt-Jakob disease (CJD), Gerstmann-Sträussler-Scheinker Syndrome (GSS), fatal insomnia and variant Creutzfeldt-Jakob disease (vCJD).

Variant Creutzfeldt-Jakob disease recently emerged in humans as an apparent result of the BSE epidemic in Britain and is believed to be caused by the consumption of food products derived from cattle infected with bovine spongiform encephalopathy or "mad cow disease".

Rendered animal byproducts have commonly been used as protein supplements in animal feed. Rendered animal byproducts are produced from meat byproduct materials that are undesirable for human consumption, such as, for example, bone, connective tissue, skin, hooves, horns, claws, fat, greaves, blood, hair, certain muscles, and combinations thereof. The byproducts are processed, or rendered, to facilitate their addition to the feed.

The emergence and spread of BSE in cattle, beginning in 1986, has been attributed in part to the consumption by livestock of feed containing BSE-contaminated rendered animal byproducts. Most cases have been reported in the United Kingdom. The export of contaminated bovine feed products from the United Kingdom worldwide indicates a possible global presence of BSE and hence the probability of the spread of vCJD. Consistent with these observations is the detection of BSE in most European countries, Japan and Israel. As of April 2002, 125 vCJD cases have been reported worldwide, primarily in the United Kingdom; however, cases have also been reported in Canada, France, Hong Kong, Ireland, Italy, and the United States.

In an effort to prevent, control, and eradicate BSE, several regulatory measures have been put in place worldwide. Many of these regulations prohibit or restrict the use of animal protein and other animal materials in feed. For example, the European Union ("EU") placed a temporary ban on the use of all processed animal proteins on certain other mammalian materials in ruminant feed. Other EU regulations prohibit the use of mammalian protein in feed, with the exception of milk and milk products, gelatin, hydrolyzed proteins, and non-bovine blood products. In the United States, regulations prohibit the use of mammalian protein in ruminant feed with the exception of milk and blood products, plate waste, and porcine or equine protein that originated from a certified non-ruminant processing facility. In Japan, both mammalian and poultry proteins are prohibited from cattle feed except milk and milk products, gelatin, collagen, and egg and egg products, while fish protein is prohibited unless it is from a certified fish-only processing facility.

Determining compliance with the above legal requirements creates the need for a test to identify the presence of animal proteins and other animal tissue components in feed materials. To assure that these legal requirements can be effectively enforced, tests are needed that can detect mammalian tissue components in concentrations as low as possible. Adequate sensitivity is desired for this purpose.

Being of a structural origin, many of the components of rendered animal byproducts are insoluble and not readily accessible for immunoassay without extensive sample processing. As such, rendered animal products must often be boiled in a salt solution as a means of extracting the reactive component or extensive purification, mainly to remove gelatin, in an attempt to obtain a functional assay. Avoiding this step would be desirable.

What is needed is an assay that overcomes the problems of low reactivity for rendered animal byproducts, thereby maximizing detection.

SUMMARY OF THE INVENTION

The present invention overcomes the problems of the prior art by providing compositions and methods for the detection of rendered animal byproduct in feed. Some compositions contain analytes comprising a component of rendered animal byproducts. Other compositions contain ligands having specificity for rendered animal byproducts. The methods include assays for the detection of rendered animal byproducts in feed and methods of production of ligands useful in the assays of the present invention. Kits for performing such assays are also provided.

In some embodiments, the ligand is an antibody produced by immunizing an animal with an analyte or antigen that exists in rendered animal byproduct. In some embodiments, the antigen is an immunogenic molecule or other substance that exists in meat and bone meal (MBM) composition. The antigen is administered to animals to produce monoclonal and polyclonal antibodies that recognize rendered animal byproduct. The antibodies are useful in assay methods for the detection of rendered animal byproduct in feed. In some embodiments, the assay is an immunoassay capable of detecting rendered animal byproduct present in low concentrations in animal feed, including concentrations of 0.1% by weight or less.

The ligands are optionally assembled in a kit with conventional assay reagents for the detection of rendered animal byproduct in a sample. In some embodiments, the kit contains either monoclonal antibodies, polyclonal antibodies, or both, and optionally includes additional components such as a standard for determining the presence or relative concentration of rendered animal byproduct in the sample and instructions for use in connection with a sample suspected of containing rendered animal byproduct.

DETAILED DESCRIPTION OF THE PREFERRED EMBODIMENTS

Figure 1:
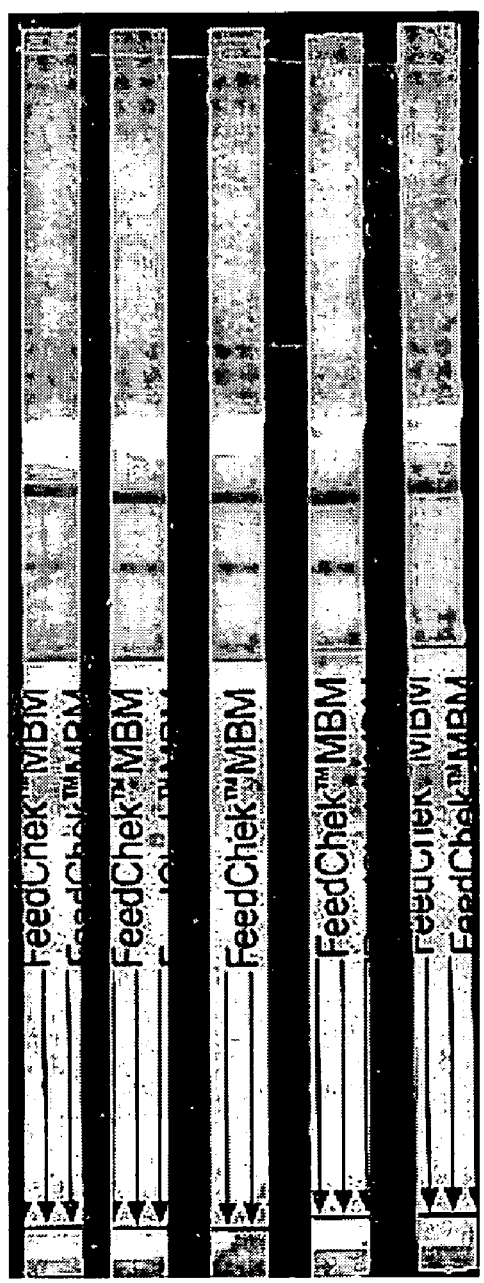
FIG. 1 is a scanned image depicting the results of testing feed containing bovine MBM on an embodiment of test strip immunoassays as described herein. Five test strips for immunoassays are depicted with the amount of bovine MBM in the feed (% w/w) shown directly above each strip. The presence of a two dark lines (running horizontally in these images) above the portion of the test strips containing lettering is a positive result. A single dark line (as seen only in 0% w/w) is a negative result.

Rendered animal byproduct analytes, ligands having specificity for the rendered animal byproduct analytes, methods for producing ligands, immunogens, assays for the detection of rendered animal byproduct in feed, and kits for performing such assays are provided.

In some embodiments, the rendered animal byproduct analyte is an antigenic meat and bone meal (MBM) composition or an immunogenic molecule or substance that exists in MBM, such as a rendered protein, peptide, proteoglycan, or polysaccharide, or a fragment of any of the foregoing. In some embodiments, the ligand is an antibody having specificity and affinity for the analyte described herein.

In some embodiments, the antibodies described herein are produced by the administration of MBM to animals under conditions effective to induce an antigenic response and are subsequently isolated from the biological fluids of the animals. In some embodiments, MBM antigens are isolated or synthesized and administered to animals to produce the antibodies reactive with MBM. In some embodiments, the antigens used are molecules or other substances that differ structurally from those actually present in rendered animal byproduct, but that contain epitopes that may be found in rendered animal byproduct or that will elicit production of antibodies that recognize rendered animal byproduct. Examples of such antigens include, but are not limited to, fragments of molecules or substances that exist in MBM or other rendered animal byproduct, synthetically produced molecules that contain epitopes found on molecules or substance that exist in MBM, including but not limited to synthetically produced molecules that contain a greater number of epitopes than those that appear on the naturally occurring molecules or substances. The antibodies described herein can be monoclonal or polyclonal antibodies and are useful in immunoassay methods for the detection of rendered animal byproduct in feed. In some embodiments, the assay is capable of detecting rendered animal byproduct at concentrations of 0.1%, by weight, or less.

Definitions

The terms "a", "an" and "the" as used herein are defined to mean "one or more" and include the plural unless the context is inappropriate.

The term "analyte" refers to any molecule, object, substance or fragment thereof to be detected or measured including, but not limited to, proteins, peptides, proteoglycans, glycoproteins, polysaccharides (including, but not limited to glycosaminoglycans), drugs, hormones, chemicals, toxins, compounds, receptors, and nucleic acid molecules.

The term "rendered" as used herein, is defined to have its broadest possible meaning to include all types of rendering processes in the animal meat processing and packaging industry, including processes that include a step of physically milling, grounding, or otherwise processing into particles of small size and heating. The purpose of heating may be, for example, to kill pathogens, to render the material more digestible, or both. One nonlimiting example of a rendering temperature is between approximately 121 and approximately 138° C., although heating temperatures vary depending on whether the heating is performed under pressure as well as the duration of heating.

The term "animal byproduct" as used herein means one or more of those parts or portions of animals, that are typically discarded during the processing of animals for the preparation of meat products from animals for human consumption. Examples include, but are not limited to bone, connective tissue (e.g. cartilage, tendons, ligaments, fascia), skin, hair, feathers, beaks, hooves, horns, claws, fat, greaves, blood, certain muscles, and combinations thereof.

The term "rendered animal byproduct" as used herein shall mean animal byproduct that has been rendered.

The term "meat and bone meal" (or "MBM") as used herein refers to a type of rendered animal byproduct. MBM is made by rendering animal byproducts of the meat packing industry. Examples of commercial providers of MBM include, but are not limited to, ConAgra Foods, (Greeley Colo.), Darling International (Irving, Tex.); Excel Corporation (Wichita, Kans.); National By-Products, (Des Moines, Iowa); and Valley Proteins, Inc., (Winchester, Va.).

The term "ligand" as used herein refers to a molecule that binds to an epitope or binding site. Examples include, but are not limited to antibodies, proteins, peptides, polypeptides, amino acids, nucleic acids, carbohydrates, sugars, lipids, organic molecules, polymers, putative therapeutic agents, and the like.

As used herein, the terms "mammalian" and "mammal" include any animal of the taxonomic class Mammalia including, but not limited to bovine, ovine, porcine, equine, murine and primate animals. In some embodiments, the mammal is a ruminant animal such as a cow.

The term "avian" refers to an animal in the class Aves. Avians are typically characterized as a warm-blooded, egg-laying vertebrate, often adapted for flying. Examples of avians include, without limitation, ratites and members of the orders Psittaciformes, Falconiformes, Piciformes, Strigiformes, Passeriformes, Coraciformes, Ralliformes, Cuculiformes, Columbiformes, Galliformes, Anseriformes, and Herodiones.

Analyte

The analyte provided herein is a molecule or substance containing a detectable component of rendered animal byproduct. The detectable component may be, for example, a molecule or substance found in rendered animal byproduct or a part of a molecule or substance found in rendered animal byproduct. In some embodiments, the analyte is a rendered animal byproduct antigen. In some embodiments, the analyte is a component of MBM, such as a rendered protein, proteoglycan, polysaccharide, or peptide, or a fragment thereof.

In some embodiments, the analyte contains one or more binding sites (e.g., epitopes) found within one or more molecules of rendered animal byproduct. The binding sites are capable of forming a bond with an antibody or other ligand. In some embodiments, the epitopes or binding sites of the analyte are or contain molecules, parts of molecules, or groups of molecules of animal byproducts that are lacking or are partially or totally cryptic or are otherwise less available or reactive for binding until the animal byproduct is subjected to the rendering process. In some embodiments, the analyte is an antigen that is absent or undetectable in non-rendered animal muscle tissue.

In some embodiments, the analyte is a detectable component of rendered animal bone or connective tissue. Examples include, but are not limited to components of bone and connective tissue that are typically found attached to or along with bones, and typically rendered with bones. Examples of such connective tissues include, but are not limited to, cartilage, tendons, ligaments, and fascia. In some embodiments, the analyte is a component of cartilage. In some embodiments, the analyte is a component of bone. In some embodiments, the analyte is a component of the extracellular matrix of cartilage or bone. In some embodiments the analyte is a protein, a proteoglycan, or a glycosaminglycan from the extracellular matrix of cartilage or bone. In some embodiments, the analyte is a detectable component of meat meal (e.g. muscle), blood meal, dried plasma and other blood products, hydrolyzed proteins, hoof meal, horn meal, milk or milk products, eggs or egg products, poultry offal meal, feather meal, dry greaves, fats and oils, fisbreal, gelatin, or combinations thereof. In some embodiments, the analyte is one or more proteins, dicalcium phosphate (e.g. hydroxyapatite) proteoglycans, or polysaccharides or components thereof. In some embodiments, the polysaccharide is a glycosaminoglycan. Examples of proteins include, but are not limited to, collagen, bone sialoprotein I (BSP-I, osteopontin), bone sialoprotein II (BSP-II), bone morphogenic proteins (BMPs), osteocalcin, osteonectin, dentin matrix protein, dentin sialoprotein, dentin phosphosialoprotein, matrix Gla protein (MGP), osteoprotegerin, osteoadherin, elastin, hyaluronic acid binding protein, laminin, osteonectin, protein or peptide components that are associated with proteoglycans (for example, linker proteins associated with aggrecans), and fibronectin. Examples of proteoglycans include, but are not limited to: aggrecans, aggregates of aggrecans (such as those often present in cartilage), PG-M proteoglycans, versicans, neurocans, brevicans, phosphacans, NG2 proteoglycans, agrins, perlecans, bamacans, serglycins, syndecans, betaglycans, cerebroglycans, OCI-5, K-glypicans, decorins, biglycans, fibromodulins, lumicans, PRELPs, keratocans, osteoadherins, epiphycan/proteoglycan Lbs, osteoglycins/mimecans, oculoglycans, opticins, and asporins. Examples of glycosaminoglycans include, but are not limited to chondroitin sulfates, heparan sulfates, keratan sulfates, dermatan sulfates, and hyaluronic acids. In some embodiments, the analyte is a water-soluble molecule or substance. In some embodiments, the analyte is chondroitin sulfate, aggrecan, osteocalcin, hyaluronic acid, or Type II collagen. In some embodiments, the analyte comprises one of the foregoing molecules or substances in the structure in which they exist after connective tissue is rendered. Examples include, but are not limited to, components that had the same molecular structure and conformation before the connective tissue was rendered and remained stable during the rendering process as well as components whose molecular structure and/or conformation are changed by the rendering process. To the extent that different types exist of the foregoing molecules (for example, collagen Types I, II, III, etc.; chondroitin sulfate A, B, C, etc.), the reference to those general terms for those molecules (e.g. "collagen", "chondroitin sulfate) is intended to include each such type and all possible combinations of types.

In some embodiments, the analyte is a water soluble molecule. Although not wanting to be bound by the following statement, it is believed that, in some embodiments, the analyte or epitope is a water-soluble animal byproduct unique to the rendering process that has not been previously described or characterized, or a component or fragment of such a byproduct.

In some embodiments, the analyte is multivalent such that a single molecule of the analyte can bind multiple antibodies of the same specificity.

Ligand

The ligand described herein includes any molecule that binds to an analyte provided above. In some embodiments, the ligand is an antibody. In some embodiments, the ligand is an antibody produced by immunizing an animal with an immunogenic MBM composition. In some embodiments, the ligand is a protein or polypeptide with binding affinity for the component. In some embodiments, the ligand is a protein with the requisite affinity, such as hyaluronic acid binding protein or certain proteins found in *Staphylococcus aureus* such as bone sialoprotein-binding protein (also known as BSP-binding protein or Bdp), collagen adhesion protein (Cna), clumping factors A and B (ClfA, ClfB), elastin binding protein (EbpS), and fibronectin binding proteins A and B (FnBPA, FnBPB). In some embodiments, the protein is an immunoglobulin. In some embodiments, the ligand is an antibody produced by immunizing an animal with an immunogenic composition containing one or more of the analytes described herein above. In some embodiments the ligand is an antibody produced by immunizing an animal with a rendered animal byproduct. In some embodiments, the ligand is an antibody produced by immunizing an animal with a molecule or substance that differs structurally from analyte, but that elicits production of antibodies that bind analytes. Examples of such molecules or substances include, but are not limited to: fragments of analytes; synthetic molecules that differ structurally from analytes but that contain one or more epitopes from the analytes; molecules that contain a deletion from, addition to, or modification or substitution of a portion of an epitope on an analyte (for example, deletion, substitution, or modification, or addition of one or more amino acids of a protein or monomers of a polysaccharide) where such deletion, addition, modification, or substitution does not impair the ability of the epitope to be recognized by an antibody that also recognizes the analyte; and constructs such as multiple antigenic peptides comprising multiple epitopes or constructs in which a portion of the detectable component is fused to an immunogenic carrier molecule such as a carrier protein. Examples of multiple antigenic peptides and carrier proteins are known in the art.

In some embodiments, the antibody lacks immunoreactivity with non-rendered animal byproduct or has a lower degree of reactivity with non-rendered animal byproduct than with rendered animal byproduct. In some embodiments, the antibody lacks immunoreactivity with animal muscle tissue. In some embodiments, the antibody lacks immunoreactivity with both non-rendered animal byproduct and with animal muscle tissue and is therefore specific for animal byproduct that has been subjected to the rendering process. In some embodiments, the antibody has greater immunoreactivity with rendered animal byproduct than with nonrendered animal byproduct.

In some embodiments, the ligand is labeled directly or indirectly to allow detection of analyte in a sample. For example, in some embodiments the labeled ligand is combined with the sample, and the labeled ligand-analyte complex is detected. In some embodiments, the ligand is labeled during ligand production, such as during peptide synthesis, or a label is conjugated to the ligand by joining it to the ligand, either covalently or non-covalently. In some embodiments, a binding molecule specific for the ligand, such as an antibody, is labeled and the complex is detected indirectly. A wide variety of labels and conjugation techniques are known and are reported extensively in both the scientific and patent literature. In some embodiments, the ligand is labeled indirectly by reaction with labeled substances that have an affinity for the ligand, such as protein A or G or antibodies specific for antibodies or other ligands. The particular label, detectable group, on conjugation technique used in the assay is not a critical aspect of the invention. Any label and any conjugation technique or other method of labeling may be used. Suitable labels include radioactive molecules, enzymes, substrates, cofactors, inhibitors, fluorescent moieties, chemiluminescent moieties, magnetic particles, and the like. The detectable group can be any material having a detectable physical or chemical property. Such detectable labels have been well-developed and, in general, any label useful in such methods can be applied to the present method. Thus, a label is any composition detectable by spectroscopic, photochemical, biochemical, immunochemical, electrical, optical, chemical or any other means. Useful labels in the present invention include fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., LacZ, CAT, horse radish peroxidase, alkaline phosphatase and others, commonly used as detectable enzymes, either in an EIA or in an ELISA), and colorimetric labels such as colloidal gold or colored glass or plastic (e.g. polystyrene, polypropylene, latex, etc.) beads. The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

In some embodiments, non-radioactive labels are attached by indirect means. In some embodiments, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. Any ligands and anti-ligands that will function can be used. In some embodiments in which the ligand has a natural anti-ligand, for example, biotin, thyroxine, and cortisol, it is used in conjunction with the labeled, naturally occurring anti-ligands. Alternatively, any haptenic or antigenic compound can be used in combination with an antibody.

In some embodiments, the ligands are conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol.

Antibodies

Antibodies are used as ligands in some embodiments. Any antibody having a binding affinity for a rendered animal byproduct may be used. In some embodiments, the antibody is a monoclonal antibody. In some embodiments, the antibody has the same specificity as monoclonal antibody ("MAb") 244C1, MAb 244C2, or MAb 244C4. In some embodiments, the antibody is MAb 244C1, MAb 244C2, or MAb 244C4. Antibodies 244C1 and 244C2 were produced by hybridomas which were deposited with the American Type Culture Collection, Rockville, Md. on or before Jan. 23, 2003. The hybridoma producing monoclonal antibody 244C1 was deposited as ATCC Accession No. PTA-4951. The hybridoma producing monoclonal antibody 244C2 was deposited as ATCC Accession No. PTA-4952.

Any of the direct or indirect labels discussed above for ligands may be used for antibodies. Examples of labels used in immunoassays are generally known to those skilled in the art and include enzymes, radioisotopes, and fluorescent, luminescent and chromogenic substances including colored particles such as colloidal gold and latex beads. In some embodiments, the antibody is conjugated with a second substance and detected with a labeled third substance having an affinity for the second substance conjugated to the antibody. For example, in some embodiments the antibody is conjugated to biotin and the antibody-biotin conjugate is detected using labeled avidin or streptavidin. In some embodiments, the antibody is conjugated to a hapten and the antibody-hapten conjugate is detected using labeled anti-hapten antibody. These and other methods of labeling antibodies and assay conjugates are well known to those skilled in the art.

Immunogens

The invention also provides immunogens that elicit production of the antibodies of the claimed invention. Any analyte or fragment of an analyte can be such an immunogen. In some embodiments, the immunogen is an isolated or purified component of rendered animal byproduct, or a fragment thereof. In some embodiments, the immunogen is an isolated or purified molecule or substance that is not found in rendered animal byproduct or that differs structurally from a component of rendered animal byproduct, but that elicits production of antibodies that bind rendered animal byproduct. Examples of such molecules or substances include, but are not limited to: fragments of components of rendered animal byproduct, optionally attached to an immunogenic carrier; synthetic molecules that differ structurally from components of rendered animal byproduct but that contain one or more epitopes found on one or more components of rendered animal byproduct; molecules that contain a deletion from, addition to, or modification or substitution of a portion of an epitope found on components of rendered animal byproduct (for example, deletion, substitution, or modification, or addition of one or more amino acids of a protein or monomers of a polysaccharide) where such deletion, addition, modification, or substitution does not impair the ability of the epitope to elicit production of antibodies that recognized one or more components of rendered animal byproduct; and constructs such as multiple antigenic peptides comprising multiple epitopes or constructs in which a portion of the detectable component is fused to an immunogenic carrier molecule such as a carrier protein. Examples of multiple antigenic peptides and carrier proteins are known in the art.

In some embodiments the immunogen will elicit production of antibodies with specificity for components of bone or connective tissue that are typically found attached to or along with bones. Examples of such connective tissues include, but are not limited to, cartilage, tendons, ligaments, and fascia. In some embodiments, the immunogen will elicit production of antibodies with specificity for one or more proteins, proteoglycans, or polysaccharides or components thereof. In some embodiments, the polysaccharide is a glycosaminoglycan. In some embodiments, the immunogen will elicit production of antibodies having the same specificity as MAb 244C1 or MAb 244C2.

Methods of Making Antibodies.

The invention also provides methods of making the antibodies of the present invention. Monoclonal and polyclonal antibodies having similar or superior sensitivity for rendered animal byproduct are produced by immunizing an animal with rendered animal byproduct or one or more of the immunogens listed above, isolation of antibodies that react with rendered animal byproduct or one of its components, and the collection and purification of the antibodies from a biological fluid such as blood in accordance with methods well known to those skilled in the art.

Any method can be used to generate antibodies, including but not limited to methods that elicit production of monoclonal antibodies. Several methods for generating monoclonal antibodies are well known to those skilled in the art. One method is a modified version of the method of Kearney, et al., J. Immunol. 123:1548–1558 (1979), which is incorporated by reference herein. Briefly, animals such as mice or rabbits are inoculated with the immunogen in adjuvant, and spleen cells are harvested and mixed with a myeloma cell line, such as P3X63Ag8,653. The cells are induced to fuse by the addition of polyethylene glycol. Hybridomas are chemically selected by plating the cells in a selection medium containing hypoxanthine, aminopterin and thymidine (HAT). Hybridomas are subsequently screened for the ability to produce anti-rendered animal byproduct monoclonal antibodies. Hybridomas producing antibodies are cloned, expanded and stored frozen for future production.

In some embodiments, antibodies are generated by immunizing an animal with an immunogenic amount of the antigen emulsified in an adjuvant such as Freund's complete adjuvant, administered over a period of weeks in intervals ranging between two weeks and 6 weeks. In a some embodiments, the method includes a first immunization in Freund's complete adjuvant and subsequent immunizations in Freund's incomplete adjuvant (at biweekly to monthly intervals thereafter) then isolating the antibodies from the serum, or fusing spleen from the animal cells to myeloma cells to make hybridomas which express the antibodies in culture. In some embodiments, test bleeds are taken at fourteen day intervals between the second and third immunizations and production bleeds at monthly intervals thereafter.

In some embodiments, conventional hybridoma techniques are employed to prepare monoclonal antibodies (MAbs) for use in the assay of the present invention. Hybridoma technology permits one to explore the entire antibody producing b-lymphocyte repertoire of the immune system and to select unique antibody producing cells that produce antibodies having unique binding characteristics. The production of monoclonal antibodies can be more controlled than production of polyclonal antisera since polyclonal antisera contain numerous antibody populations each having varying specificity and sensitivity characteristics that are the products of numerous responding b-cell clones. MAb reagents are also homogeneous with a defined specificity. The use and appropriate selection of hybridoma cell lines provides MAb reagents that offer unique performance characteristics to the test system and consistency of the methods that utilize them. The invention is not limited to use of monoclonal antibodies, however, and polyclonal antibodies or any other type of antibodies may be used.

In some embodiments, hosts responding to the immunization protocol are selected as splenocyte (or lymphoid cell) donors for hybridoma production. In some embodiments, hybridomas are produced by fusing a culture of immune lymphocytes fused with modified myeloma cells, for example by using polyethylene glycol (PEG) with modified myeloma cells in a defined tissue culture medium, such as HAT (hypoxanthine, aminopterin, thymidine). This process is capable of providing a variety of fusion products, such as s-s, s-m, and m-m (with s=splenocyte and m=myeloma cell). In some embodiments, the s-s fusion product and m-m fusion product both have a very short lifetime while the s-m fusion product (or hybridoma) survives in tissue culture and retains the antibody-producing characteristics of the splenocyte parent as well as the high rate of growth and relative immortality of the myeloma cell parent. These hybridoma cell lines replicate readily in culture producing daughter cells that provide a reproducible, homogeneous, and consistent supply of the monoclonal antibody of the present invention. Selection of the appropriate cell line provides the monoclonal antibody of some embodiments of the present invention. Monoclonal antibodies may also be made by using other types of cells that have been genetically engineered to express immunoglobulins and to produce antibodies. Any method of making antibodies may be used.

Assays

Assays employing a ligand specific for one or more components of rendered animal byproduct or any analyte described above are also provided. The assays are useful for detecting the presence or amount of rendered animal byproduct in one or more samples. In some embodiments, the sample is animal feed. In some embodiments, the assay is an immunoassay that employs an antibody specific for a rendered animal byproduct analyte or an epitope found in rendered animal byproduct. In some embodiments, the assay uses a non-immunoglobulin protein with binding affinity for a component of rendered animal byproduct analyte, such as hyaluronic acid binding protein or certain proteins found in *Staphylococcus aureus* such as bone sialoprotein-binding protein (also known as BSP-binding protein or Bdp), collagen adhesion protein (Cna), clumping factors A and B (ClfA, ClfB), elastin binding protein (EbpS), and fibronectin binding proteins A and B (FnBPA, FnBPB).

In embodiments involving immunoassays, the antibody and, optionally, assay conjugates, may be employed in any heterogeneous or homogeneous, sandwich or competitive immunoassay for the detection of rendered animal byproduct. In some embodiments the antibody is labeled (directly or indirectly) with a detectable label, coupled to a solid phase, or both. Any method of labeling or coupling may be used. Methods for coupling antibodies to solid phases are well known to those skilled in the art. In accordance with the immunoassay method, the sample containing the analyte is reacted with the antibody for a sufficient amount of time under conditions that promote the binding of antibody to rendered animal byproduct in the sample. It will be understood by those skilled in the art that the immunoassay reagents and sample may be reacted in different combinations and orders. A physical means is employed in some embodiments to separate reagents bound to the solid phase from unbound reagents. Examples of such means include, but are not limited to filtration of particles, decantation of reaction solutions from coated tubes or wells, magnetic separation, capillary action, and other means known to those skilled in the art. It will also be understood that a separate washing of the solid phase may be included in the method.

In some embodiments, the ligand is immobilized on a solid phase to facilitate detection. Any solid phase that will allow immobilization may be used. It will be understood by those skilled in the art that examples of solid phases include latex, polystyrene, polyethylene, polypropylene, polycarbonate or any solid plastic material in the shape of test tubes, beads, microparticles, dip-sticks or the like. A solid phase also includes glass beads, glass test tubes and any other appropriate shape made of glass. In some embodiments, the solid phase is a nitrocellulose strip.

After reaction, the existence, concentration, or both of the analyte is determined by the signal generated by the label. The presence or location of the signal may be an indicator. In some embodiments involving a sandwich assay, the ligand is fixed to a substrate and the sample is contacted with the substrate under conditions effective to cause the ligand to bind analyte in the sample. The bound ligand is also contacted (either subsequently or simultaneously with its contact with the sample) with unbound ligand that is labeled under conditions effective to cause the labeled ligands to bind the analyte that has already bound to the fixed ligand. The substrate is then washed to remove any unbound ligand and the presence and/or concentration of the analyte is indicated by the presence and/or strength of the label signal. In some embodiments involving a direct assay, the sample is placed under conditions effective to cause any analyte in the sample to become fixed on a substrate. The substrate is then contacted with labeled ligand under conditions effective to cause binding of the ligand to any bound analyte. The substrate is then washed to remove any unbound ligand and the presence and/or concentration of the analyte is indicated by the presence and/or strength of the label signal.

Some competitive assays involve placing a sample suspected of containing an analyte together with an analyte analog conjugated to a label, and the competition of these species for a limited number of binding sites provided by a ligand immobilized on a solid phase. The analyte analog also has a binding affinity for the ligand. Due to competition between any analyte in the sample and analyte analog-signal conjugate for ligand binding sites, an increase in analyte concentration in the sample causes a decrease in the amount of immobilized ligand available to bind the analyte analog-enzyme conjugate, thus decreasing the amount of label that becomes immobilized and, in turn, decreasing the observed signal in the location in which the immobilized ligand is located. The existence, strength, or both label can then be measured to determine the presence on the solid phase, quantity of the solid phase, or both. The decrease in signal indicates the presence and, optionally, concentration of analyte in the sample. In some embodiments of competitive assays, the assay is as described above except that the ligand is labeled and the analyte analog is immobilized on the solid phase, again resulting in an assay in which an increase in analyte concentration in the sample causes a decrease in signal on the solid phase.

The foregoing are simply examples of assays and any assay method may be used, including other types of direct and indirect assays as well as competitive assays.

Detection of labels may occur by any method. Examples of known methods include, but are not limited to immunoblotting, western blot analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. Any means may be used to detect labels. Thus, for example, where the label is a radioactive label, examples of means for detection include a scintillation counter or photographic film as in autoradiography. Where the label is a fluorescent label, it may be detected, for example, by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels are detected, for example, by providing appropriate substrates for the enzyme and detecting the resulting reaction product. Finally, simple calorimetric labels may be detected, for example, by observing the color associated with the label. Thus, in various dipstick assays, conjugated gold often appears pink, while various conjugated beads appear the color of the bead.

Examples of detection methods include but are not limited to a direct or indirect enzyme-linked immunosorbent assay (ELISA) using a secondary antibody such as a peroxidase-conjugated goat anti-mouse antibody or a direct or indirect immunofluorescence assay using a secondary antibody such as a fluorescein isothiocyanate (FITC)-conjugated goat anti-mouse antibody.

In some embodiments, the concentration of rendered animal byproduct in the sample is determined either by comparing the intensity of the color produced by the sample to a color card or by using a reflectometer.

In some embodiments the resulting reaction mixture, or combination of ligand and sample, is prepared in a solution that optimizes ligand-analyte binding kinetics. An appropriate solution is an aqueous solution or buffer. The solution can be provided under conditions that will promote specific binding, minimize nonspecific binding, solubilize analyte, stabilize and preserve reagent reactivity, and can contain, for example, buffers, detergents, solvents, salts, chelators, proteins, polymers, carbohydrates, sugars, and other substances known to those skilled in the art.

In some embodiments, the ligands of the invention are used to detect targets extracted into solution from a solid material. In some embodiments, a sample of the solid material is extracted with an aqueous liquid, an organic solvent or a critical fluid and the resulting supernatant is contacted with the ligand. Any solid substances may be used. Examples of solid samples include feed products, particularly those that are suspected of having been exposed to rendered animal byproduct.

The reaction mixture solution is reacted for a sufficient amount of time to allow the ligand to react and bind to the analyte to form an ligand-analyte complex. Any time period may be used, although the shortest amount of reaction time that results in binding is sometimes desired to minimize the time required to complete the assay. In some embodiments, the reaction time period for an immunochromatographic strip test is less than or equal to 20 minutes or between approximately one minute and 20 minutes. In some embodiments, the reaction time is less than five minutes. In some embodiments, the reaction time is less than three minutes. By optimizing the reagents, binding in some embodiments can be substantially completed as the reagents are combined.

The reaction is performed at any temperature at which the reagents do not degrade or become inactivated. In some embodiments, the temperature is between approximately 4° C. and 37° C. In some embodiments, reaction temperature is ambient or room temperature (approximately 25° C.).

In some embodiments the assay is performed on strip tests comprised of multiple porous components, membranes and filters, through which liquid sample is drawn by capillary action. Analyte in the sample reacts with the test reagents contained within the test strip as it traverses the length of the strip. In some embodiments in which the goal is to detect an analyte (such as a protein, polysaccharide, or proteoglycan) in feed, the feed is ground into a powder and the analyte is extracted from the powder with a liquid that is then separated from the solid material and assayed using the test. The liquid is applied to the chromatographic strip, and the analyte migrates toward the distal end of the strip. As it migrates down the strip, the analyte reacts with reagents applied to or immobilized on the strip causing a detectable signal product. Detection of the signal indicates the presence of the analyte in the sample.

The assays of the present invention are capable of detecting rendered animal product such as meat and bone meal when present in compositions (including, for example, animal feed), at concentrations lower than those at which other assays can detect rendered animal product. In some embodiments, the assays detect rendered animal product in concentrations as low as about 0.50% and above by weight. In some embodiments, the assays detect rendered animal product in concentrations as low as about 0.10% and above by weight. In some embodiments, the assays detect rendered animal product in concentrations as low as about 0.05% and above by weight. In some embodiments, the assays detect rendered animal product in concentrations as low as about 0.01% and above by weight. In some embodiments, the assays detect rendered animal product in concentrations as low as about 0.005% and above by weight. In some embodiments, the assays detect rendered animal product in concentrations as low as between about 0.10% and about 0.50% by weight in a composition. In some embodiment, the assays detect rendered animal product in concentrations as low as between about 0.05% and about 0.10% by weight. In some embodiments, the assays detect rendered animal product in concentrations between about 0.01% and about 0.05% by weight. In some embodiments, the assays detect rendered animal product in concentrations between about 0.01% and about 0.005% by weight.

Assays Involving Tests for More Than One Analyte

In some embodiments, the assay includes additional steps that allow determination of whether detected rendered animal byproduct or other animal materials present in a composition are from a specific taxonomic classification or group of taxonomic classifications. In such embodiments, the assay includes reacting the sample with a at least a second ligand that has binding affinity for a second analyte. Any second assay may be used. In some embodiments, the second analyte is a molecule having binding sites that are present and capable of binding in animal material derived from animals of one taxonomic classification or group of taxonomic classifications but that are absent, are incapable of binding, or have a measurably lower affinity in animal material derived from animals of one or more different taxonomic classification or groups of taxonomic classifications. In some embodiments, the second ligand has binding affinity for an epitope or binding site that is present and capable of binding in animal material derived from mammals but is absent, is incapable of binding, or has a measurably lower affinity in animal material derived from other vertebrates. In some embodiments, the second ligand has binding affinity for an epitope or binding site that is present and capable of binding in animal material derived from mammals but is absent, is incapable of binding, or has a measurably lower binding affinity in animal material derived from avians. In some embodiments, the second ligand has binding affinity for an epitope ruminant mammals but is absent, is incapable of binding, or has a measurably lower binding affinity in animal material derived from one or more groups other than ruminant mammals. In some embodiments, the second ligand has binding affinity for an epitope or binding site that is present and capable of binding in animal material derived from one taxonomic family or group of taxonomic families of mammals but is absent, is incapable of binding, or has a measurably lower binding affinity in animal material derived from other taxonomic families of mammals. In some embodiments, the second ligand has binding affinity for an epitope or binding site that is present and capable of binding in animal material derived from one genus or group of genera of mammals but is absent, is incapable of binding, or has a measurably lower binding affinity in animal material derived from other genera of mammals. In some embodiments, the second ligand has binding affinity for an epitope or binding site that is present and capable of binding in animal material derived from one species or group of species of mammals but is absent, is incapable of binding, or has a measurably lower binding affinity in animal material derived from other species of mammals, optionally including other species in the same family or the same genus as the first species. In some embodiments, the second ligand has binding affinity for an epitope or binding site that is present and capable of binding in animal material derived from one or more populations, subspecies, or varieties of a given species but is absent, is incapable of binding, or has a measurably lower binding affinity in animal material derived from other populations, subspecies, or varieties of that species. By "measurably lower binding affinity" in a taxon or group of taxa it is meant that the binding affinity differs to such extent from that of another taxon or group of taxa that an observable difference in the results of an assay occurs. The foregoing are simply examples of ligands and any combination binding affinities and absence of binding affinities is within the present invention.

In some embodiments, the second ligand has binding affinity for molecules or substances of a type that are present in one taxonomic classification but absent in other taxonomic classifications. In some embodiments, the second ligand has binding affinity for epitopes or binding sites that are present upon the molecules or substances as they exist in one taxa or group of taxa but that are absent or have a measurably lower binding affinity upon the molecules or substances as they exist in other taxa. In some embodiments, the second ligand is an antibody having specificity for an epitope that is present on a protein or proteoglycan molecule as it exists in one taxa or group of taxa, but absent from or cryptic upon the analogous protein or proteoglycan molecule as it exists in other taxa. Any protein, polysaccharide, proteoglycan, or other molecule present in any animal tissue or rendered animal product may be used. In some embodiments, troponin molecules are used. In some such embodiments of the present invention, a ligand has binding affinity for a mammalian ST troponin molecule and/or a mammalian FT troponin molecule, and lacks binding affinity for an avian troponin I molecule. In some embodiments, a ligand has binding affinity for a particular region within a FT or ST troponin molecule, which region is conserved between several mammalian troponin I molecules, but not conserved between mammalian and avian troponin I molecules. In some embodiments, a ligand is specific for cow and pig FT and/or ST troponin molecules and not specific for avian troponin I molecules. Accordingly, in some embodiments, a ligand is provided that is specific for a ST troponin molecule and/or a FT troponin molecule derived from a cow, a horse or a pig, or any combination thereof, and is not specific for a troponin I molecule derived from a chicken or quail.

Any effective combination of methods, materials, and process steps may be used in the second assay including, but not limited to, the combinations and embodiments disclosed above in the description of the first assay of the present invention. In some embodiments, the second assay is performed separately from the first assay, using different materials (for example, different substrates and labels). In some embodiments, the reactants are prepared so that the two assays are performed essentially simultaneously. In some embodiments, both ligands are located upon a single solid phase so that the sample will react with both ligands. In some embodiments in which both assays are sandwich immunoassays, each ligand is fixed at different locations or zones on a test strip such as a nitrocellulose test strip. The first ligand is an antibody having specificity for a component of rendered animal byproduct and the second ligand is an antibody having specificity for epitope that is present and capable of binding upon a mammalian form of a protein present in rendered animal byproduct (for example, a troponin) but that is either absent or incapable of binding upon the avian form of that protein. The sample is contacted with both of the bound ligands as well as unbound molecules of each type of ligand under conditions effective to cause binding of the bound and unbound ligands to any analytes to which the have an affinity that are contained in the sample. Both of unbound ligands are labeled such that they generate a detectable signal. After providing an opportunity for binding to occur, the absence of any signal in either zone indicates the absence of rendered animal byproduct. The presence of a signal in the zone containing the bound first ligand along with the absence of a signal in the zone containing the bound second ligand indicates the presence of rendered animal byproduct of a nonmammalian source. The presence of a signal in both zones indicates the presence of rendered animal byproduct of a mammalian source. The foregoing is simply an example of a combination of two assays, and any combination is possible.

Although the discussion above refers to a "second" assay, embodiments also exist in which more than two assays are performed. Examples include embodiments in which three, four, five, six, or more assays are performed. In some embodiments, multiples assays using multiple different ligands are performed simultaneously. In some embodiments, an assay for rendered animal byproduct is combined, for example upon a test strip, with multiple assays useful for analytes from a variety of taxa or groups of taxa. In some embodiments, an assay for rendered animal byproduct is combined with separate assays specific for ruminant animal byproduct, avian animal byproducts, porcine animal byproduct, or a combination of two or more of the foregoing. In some embodiments, additional assays serve to identify specifically the substances causing a positive result in one test. In some embodiments, additional assays for substances such as fish meal, bovine milk, and mammalian blood meal are used. Optionally, two or more assays in the group are combined into to test strips. In some embodiments, a group of test strips each contain two or more separate tests, for example, three test strips that contain a total of nine assays. Any effective combinations of tests may be used.

Assay Kit

An assay kit for the detection of rendered animal byproduct in a sample contains one or more of the ligands described above. In some embodiments, the assay kit is an immunoassay kit containing one or more antibodies specific for the rendered animal byproduct analyte provided herein. The kit may additionally contain one or more of the following, and any combination thereof: equipment for obtaining the sample, a vessel for containing the reagents, a timing means, a buffer for diluting the sample, and a colorimeter, reflectometer, or standard against which a color change may be measured. In some embodiments, the antibody is collectively assembled in a kit with conventional immunoassay reagents for detection of rendered animal byproduct. The kit may optionally contain both monoclonal and polyclonal antibodies and a standard for the determination of the presence of rendered animal byproduct in a sample. The kit containing these reagents provides for simple, rapid, on site detection of rendered animal byproduct.

In some embodiments, the reagents, including the antibody are dry. Addition of aqueous sample to the strip results in solubilization of the dry reagent, causing it to react.

The invention will be described in greater detail by way of specific examples. The following examples are offered for illustrative purposes, and are intended neither to limit nor define the invention in any manner.

EXAMPLE 1

Preparation of Monoclonal Antibodies to MBM

Monoclonal antibodies (MAbs) were generated by a modified version of the method of Kearney et al., *J. Immunol.* 123:1548–1558 (1979). A crude 10% (w/v) MBM extract was prepared by adding 2.5 g MBM from a commercial source to 25 mL of 50 mM Tris, pH 8, containing 10 mM EDTA. The extract was boiled and centrifuged at 5000×g for 30 min, then the supernatant from this solution was diluted in complete Freunds adjuvant to prepare a 1:1 solution of supernatant: adjuvant. Three month old Swiss Webster mice were immunized by injection 0.2 ml solution of supernatant: adjuvant. Mice received two booster injections of the same extract/adjuvant at one month and two months after initial injection. At three months after initial injection spleen cells were harvested from the mice and mixed with myeloma cell line P3X63Ag8,653. The cells were induced to fuse by the addition of polyethylene glycol. Six (6) cell fusions were performed Hybridomas were chemically selected by plating the cells in a selection medium containing hypoxanthine, aminopterin and thymidine (HAT). Hybridomas were subsequently screened for the ability to produce anti-MBM monoclonal antibodies, as determined by a direct bind ELISA. Hybridomas producing anti-MBM antibodies were cloned, expanded and stored frozen for future production. Such MAbs were designated 244C1, 244C2, and 244C4.

EXAMPLE 2

Reactivity of MAb with MBM and various tissues and proteins

Tissue, Protein, and MBM Sample Preparation.

Bovine meat and bone meal samples were obtained from a commercial meat rendering operation. Typical process temperatures were between about 121 and about 138° C.

Chicken muscle (breast), bovine muscle (leg), and bovine connective tissue were obtained from a grocery store. (Bovine connective tissue was obtained by purchasing a leg bone, removing "gristle" from the leg bone and cutting away all muscle from the cut samples and using the gristle as bovine connective tissue). Samples were stored frozen and thawed prior to use. Dried pig ear and bovine hoof were obtained from a commercial supplier. Prior to processing, pig ears and bovine hoof were ground to a powder and wet with water to make a thick slurry. Tissue samples (without homogenization) were placed in loosely wrapped foil packets inside an autoclave bag and autoclaved for 2 hours at 121° C. (slow exhaust), except that for dried pig ear, one sample was autoclaved, while the other was not. During autoclaving most of the fat content drained from the foil packets and was discarded. After autoclaving, the samples were dried overnight at 80° C. in a forced air oven. Samples that had not previously been ground were then finely ground using a mortar and pestle and stored at room temperature prior to use.

Type I and II collagens (chicken) were obtained from Chemicon (Temecula, Calif.; CC090 and CC092, respectively). Type III collagen (bovine, C-3511), gelatin (bovine, G-9382), elastin (bovine, E-6527), actin (bovine, A-3653), and myosin (chicken, M-7266) were obtained from Sigma (St. Louis, Mo.). KNOX Gelatin (Nabisco, Inc.) was purchased at a grocery store. Troponin I (bovine) was obtained from Life Diagnostics (West Chester, Pa.; Cat No. 3310). Keratin powder was obtained from ICN Biomedicals, Inc., (Aurora Ohio, Catalog No. 902111).

Extraction Procedures

Samples were extracted with a 10-fold excess volume of 1M NaCl (i.e. 1 g tissue or protein and 10 mL 1M NaCl) by hand shaking. After 1 min of settling, the supernatant was used for sample analysis. The MBM extract was tested by a BCA protein assay (Pierce, Rockford, Ill. Cat No. 23235) and found to contain 10-20 mg/mL of dissolved protein.

Sandwich ELISA Procedures.

Figure 2:
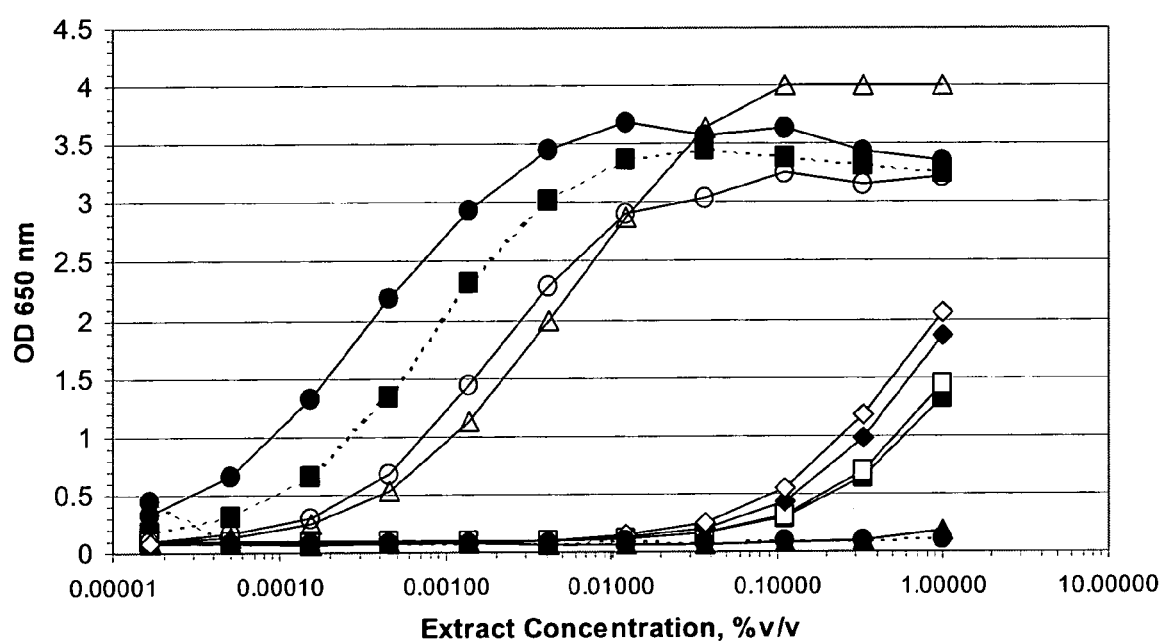
FIG. 2 is a graph depicting the results of a sandwich ELISA of bovine MBM (BMBM) and various animal tissue fractions using an antibody as described herein. "OD" in the y-axis legend refers to optical density. Key to plots: BMBM plot—closed square data points and a dashed line; bovine muscle—closed square data points, solid line; chicken muscle—open square data points; pig ear—closed circle data points, solid line; pig ear (not autoclaved)—open circle data points; bovine hoof—closed triangle data points; bovine connective tissue—open triangle data points; keratin powder—closed diamond data points; keratin powder (boiled)—open diamond data points; gelatin: closed circle data points, dashed line.

Extracts of bovine MBM, beef muscle, chicken muscle, pig ear (both autoclaved and non autoclaved), bovine hoof, bovine connective tissue, gelatin (KNOX), keratin powder were prepared using the procedures above. Some extracts of keratin powder were boiled in a closed container for 10 minutes; other keratin powder extracts were not. Extracts were then diluted with PBS-T (phosphate buffered saline containing 0.05% TWEEN 20) containing 0.1% BSA (assay buffer) to prepare dilutions containing extract in amounts of 0.00001%, 0.00010%, 0.00100%, 0.01000%, 0.10000%, 1.00000%, and 10.00000% (each percentage v/v) for each extract. Monoclonal antibody (MAb) 244C1 was coated on microtiter plates at 2.5 µg/mL in PBS. The plates were incubated overnight at 4° C. then washed with PBS-T. The plates were blocked with 100 µL Stabilcoat (Surmodics, Inc. Eden Prarie, Minn.) overnight at 4° C. The plates were washed with PBS-T. Diluted extracts of each concentration (100 µL) were incubated on plates for 1 h at room temperature and the plate was then washed. One hundred microliters per well of MAb 244C1 conjugated to horseradish peroxidase diluted in assay buffer was added and the plate was incubated for one hour at room temperature. The plate was then washed. One hundred microliters per well of TMB (available from Moss Inc., Pasadena, Md.) was added to the plates and color development was measured at 650 nm using a microtiter plate reader. Results are presented in FIG. 2.

Analysis of heat-treated tissue fractions have revealed that the reactivity is confined to those portions of tissue containing a high amount of connective tissue. Results indicate that pure bone and pure muscle (meat) are non-reactive.

Direct Bind ELISA Procedures.

Figure 3:
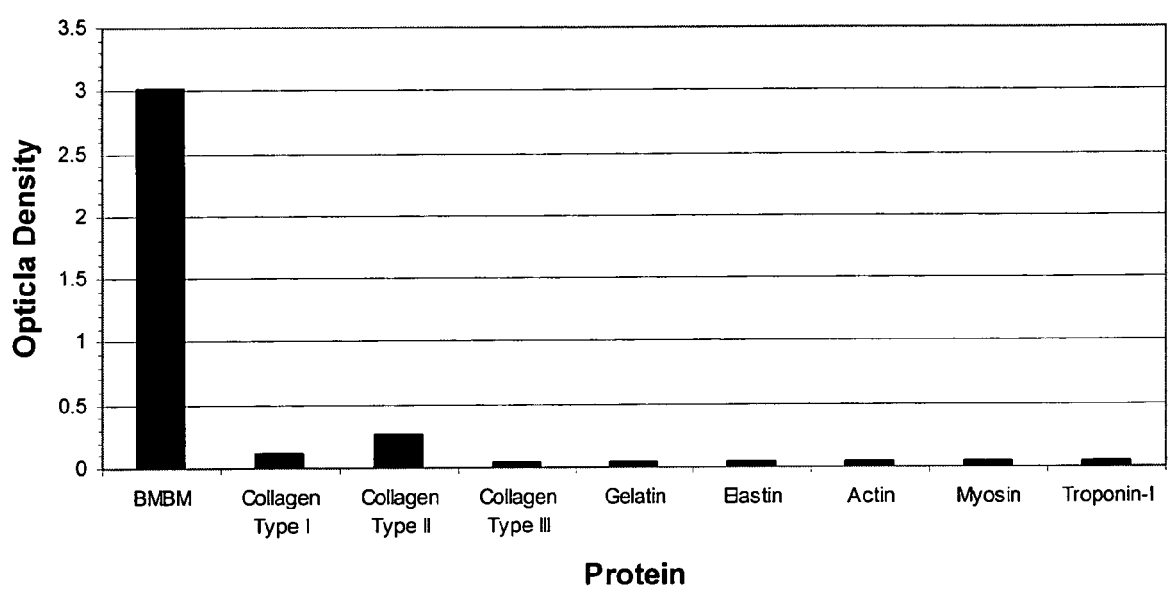
FIG. 3 is a bar graph depicting relative direct bind ELISA reactivity of anti-MBM MAb 244C1 to MBM and various heat-denatured proteins expected to be found in MBM.

The Collagen Type I, Collagen Type II, Collagen Type III, gelatin (Sigma), elastin, actin, myosin, and troponin I described above were received from the vendor either liquid (approximately 1 mg/mL) or as lyophilized powders. The powders were reconstituted to concentrations of approximately 0.5 mg/mL to about 5.0 mg/mL as indicated by the manufacturer. Each protein solution (200 µL) was boiled in a closed container for 20 minutes then further diluted in 0.1 M carbonate buffer, pH 9.6, to 5 µg/mL. 1 g MBM was added to 10 mL of PBS containing 0.3% SDS. The solution was boiled for 20 min, then centrifuged at 250×g for 10 min. The supernatant was tested by a BCA protein assay and found to contain 3.7 mg/mL dissolved protein. The supernatant was then diluted to 5 µg/mL in 0.1 M carbonate buffer. The dilute MBM extract and dilute protein solutions were each subjected to direct bind ELISA using the following procedures. Microtiter plates were coated with 100 µL/well for each protein solutions and the MBM extract. The plates were incubated overnight at 4° C. and then washed with PBS containing 0.05% (v/v) Tween 20 (PBS-T). Plates were blocked with 120 µL PBS-T containing 1% casein (PCT) for one hour at room temperature and washed with PBS-T. One hundred microliters per well of hybridoma MAb purified (using the Protein A method) or supernatant were added and the plates incubated for 1 hour at room temperature and then washed. Rabbit anti-mouse IgG conjugated to horseradish peroxidase diluted in PCT was added to the wells and the plate was incubated for one hour at room temperature. The plates were washed. One hundred microliters per well of TMB (Moss, Inc. Pasadena, Md.) were added to the plates and color development was measured at 650 nm using a microtiter plate reader. Results are presented in FIG. 3.

Reactivity to purified, heat denatured proteins is very low, as compared to the level of sensitivity observed in MBM using the antibodies. In addition, reactivity to the skeletal muscle proteins troponin I, myosin, and actin were very low.

EXAMPLE 3

Preparation of a Lateral Flow Immunochromatography Assay

MAb 244C1 (test line) was sprayed at 1 mg/mL in PBS onto nitrocellulose membrane (Millipore, Bedford, Mass. Cat No. HF07054500) using a Biodot XYZ3000-dispensing platform sprayer (Irvine, Calif.). Goat anti-mouse IgG (Lampire Biological Labs, Pipersville, Pa.) was sprayed as the control line at 1 mg/mL in PBS. MAb 244C2 was conjugated to colloidal gold (BBI, Cardiff, UK; 40 nm) using standard methods (Beesley, J. E. (1989). *Colloidal gold: A new perspective for cytochemical marking*. Oxford University Press, New York) and dried onto polyester pads (Reemay 2033, Ahlstrom, Mt. Holly Springs, Pa.). Sprayed nitrocellulose membrane and MAb-gold-treated polyester pads were laminated onto plastic backing. A sample filter paper was placed below the gold pad at the sample application end of the strip. A wicking paper was placed above the membrane to facilitate continuous capillary flow. The assembly was cut into test strips using a guillotine cutter. For sample analysis, 500 µL of liquid sample was placed into a 1.8 mL microcentrifuge tube. The test strip was placed into the vial where only the sample filter pad contracted the sample. The test strip was allowed to develop in the sample for ten minutes. Following ten minutes, the test strip was removed from the sample and the results were interpreted. If two lines were present, the result was positive. If one line were present (at the control zone), the result was negative.

Samples having different known concentrations of MBM were applied to test strips pursuant to this procedure. These assays showed high levels of sensitivity toward MBM (at least less than 0.1% (w/w) in feed) (FIG. 1).

EXAMPLE 4

Determination of Antibody Tissue Reactivity to Cartilage

Fresh whole pig ear (raw) was obtained from Galvinell Meat Co. (Conowingo, Md.) within 24 hours after slaughter. Within 48 hours after slaughter, portions of the pig ear were skinned and portions of the cartilage were removed such that separate samples of whole ear, skin, and cartilage were obtained. Portions of each of the three sample types were separately wrapped loosely in a aluminum foil packets that were, in turn, placed in 4 dram vials, and autoclaved at 132° C. for 2 hours. The wrapped packets were positioned above the bottom of the vials so that fat and other drippings would drain from the packets Other portions of each of the three sample types were not autoclaved. Raw and autoclaved samples of whole ear, skin, and cartilage were diced into small, roughly cubical sections (5–20 mm$^2$ area per side of each cubical section). Extracts from each diced tissue were made by placing the diced tissue in a 1 molar sodium chloride solution in an amount such that each solution contained 1 gram of diced tissue in every 10 milliliters of combined solution and tissue of NaCl solution) and shaking the combined sample and NaCl solution by hand for 15 seconds. Soluble protein content was determined by BCA protein assay. Extracts were then diluted to 10% concentration, then further diluted to desired protein concentration, all dilutions using assay buffer (phosphate buffered saline containing 0.1% bovine serum albumin and 0.1% TWEEN 20).

Bovine MBM (BMBM) samples were extracted with a 10-fold excess volume of 1M NaCl (i.e. 1 g tissue or protein and 10 mL 1M NaCl) by hand shaking. Extracts were then subject to the same extraction and dilution procedure.

Figure 4:
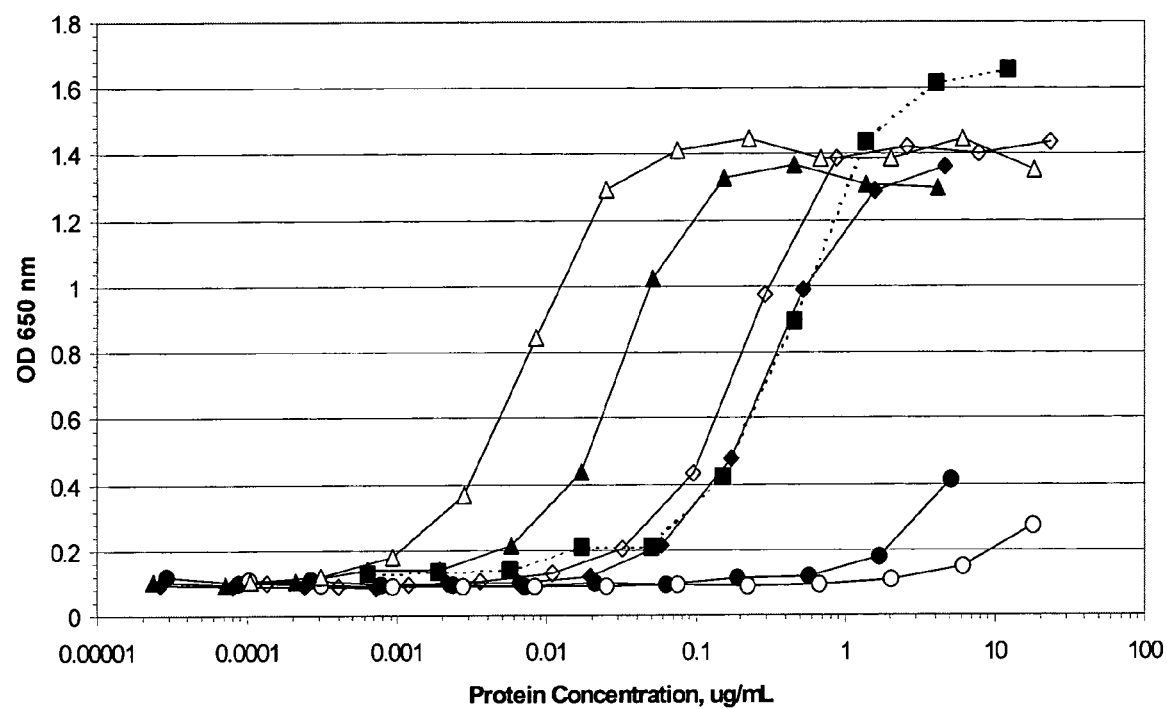
FIG. 4 is a graph depicting reactivity of various pig ear tissues using anti-MBM MAbs in a sandwich ELISA of bovine MBM (BMBM) and various animal tissue fractions using an antibody as described herein. "OD" in the y-axis legend refers to optical density. Key to plots: BMBM—closed square data points, dashed line; skin (raw)—closed circle data points; skin (autoclaved)—open circle data points; cartilage—closed triangle data points; cartilage (autoclaved)—open triangle data points; whole ear (raw)—closed diamond data points; whole ear (autoclaved)—open diamond data points.

The extracts were then tested for reactivity with Monoclonal antibody (MAb) 244C1 by sandwich ELISA. MAb 244C1 was coated on microtiter plates at 2.5 µg/mL in PBS. The plates were incubated overnight at 4° C. then washed with PBS-T. The plates were blocked with 200 µL phosphate buffered saline containing 0.1% bovine serum albumin and 0.1% TWEEN 20 at room temperature for one hour. The plates were washed with PBS-T. Diluted extracts of each tissue concentration (100 µL) were incubated on plates for 1 hour at room temperature and the plate was then washed. One hundred microliters per well of MAb 244C1-biotin conjugate diluted in assay buffer was added and the plate was incubated for one hour at room temperature. The plate was then washed. One hundred microliters per well of streptavidin-horseradish peroxidase diluted in assay buffer was added and the plate was incubated for one hour at room temperature. TMB was added to the plates and color development was measured at 650 nm using a microtiter plate reader. FIG. 4 contains the results.

Whole ear (raw and autoclaved) was reactive in the sandwich ELISA. Skin and cartilage isolated from the whole ear were tested separately. Raw and autoclaved cartilage tissue were both highly reactive whereas neither raw nor autoclaved skin tissue was reactive. Furthermore, autoclaving the cartilage tissue resulted in a significant increase in ELISA reactivity.

EXAMPLE 5

Determination of Antibody Reactivity to Various Proteins

Aggrecan (bovine, catalog No. A-1960), laminin (human, catalog No. L-6274) and fibronectin (bovine, catalog No. F-1141) were obtained from Sigma. Collagen type II, troponin-I, collagen type III, and elastin were obtained from the same sources indicated above in EXAMPLE 2. Aggrecan, collagen types I and II, elastin, laminin, and fibronectin (0.1 mg/mL) were obtained and extracted. Samples were extracted using the procedures set forth for sandwich ELISA in EXAMPLE 2. Some of each type of extract (except troponin) was boiled for 15 min using the procedures set forth in Example 2; some extract was not boiled. Bovine MBM was extracted 10-fold using the extraction procedures set forth in Example 2 and tested by a BCA protein assay for soluble protein. No boiled MBM extract was prepared.

Boiled and unboiled extracts of aggrecan, Types II and III Collagen (separately), elastin, laminin, and fibronectin, as well as unboiled extracts of BMBM and Troponin-I were tested for reactivity with Monoclonal antibody (MAb) 244C1 by sandwich ELISA using the same procedures set forth in EXAMPLE 5, above. 100 microliters per well of TMB was added to the plates and color development was measured at 650 nm using a microtiter plate reader.

Figure 5:
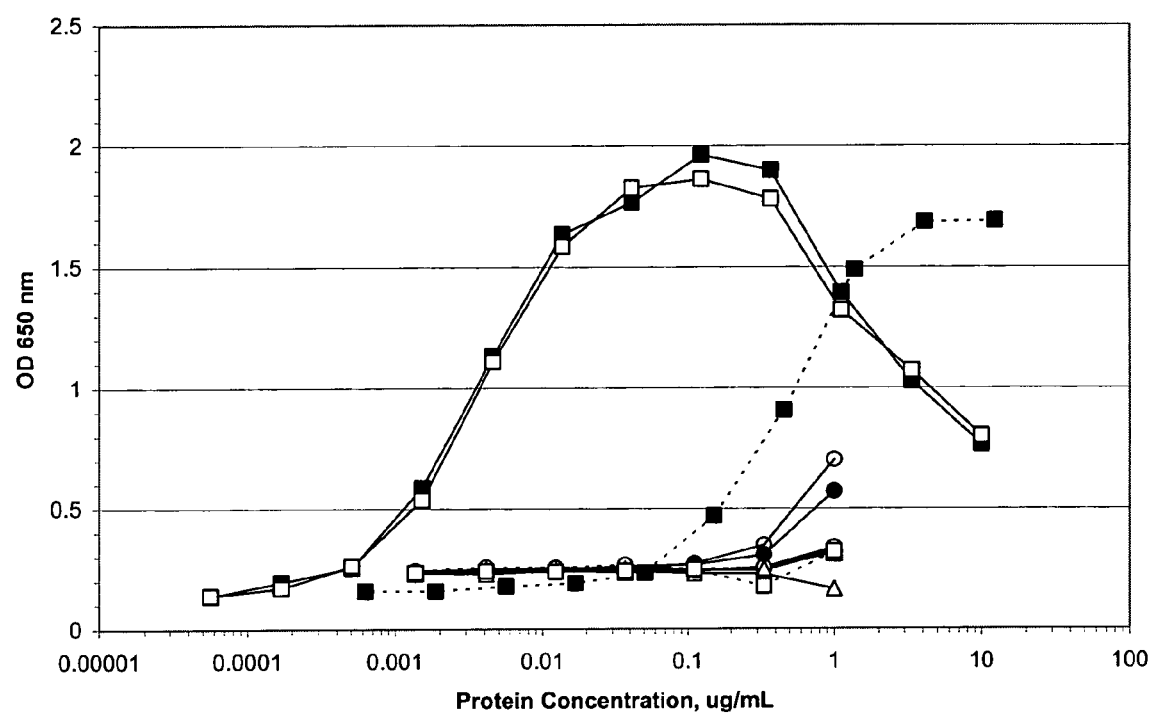
FIG. 5 is a graph depicting reactivity of various connective tissue proteins using anti-MBM MAbs in a sandwich ELISA of bovine MBM and various proteins and proteoglycans using an antibody as described herein. "OD" in the y-axis legend refers to optical density. Key to plots: BMBM—closed square data points, dashed line; aggrecan—closed square data points, solid line; aggrecan (boiled)—open square data points; collagen type II—closed circle data points, solid line; collagen type II (boiled)—open circle data points, solid line; collagen type III—closed triangle data points, solid line; collagen type III—open triangle data points, solid line; elastin—closed diamond data points; elastin (boiled)—open diamond data points; laminin—closed circle data points, dashed line; laminin (boiled)—open circle data points, dashed line; fibronectin—closed triangle data points, dashed line; fibronectin (boiled)—open triangle data points, dashed line; troponin I—open square data points, dashed line.

The results are presented in FIG. 5. Aggrecan (boiled and non-boiled) showed significant reactivity with MAb 244C1. Other analytes tested did not show significant reactivity.

EXAMPLE 6

Figure 6:
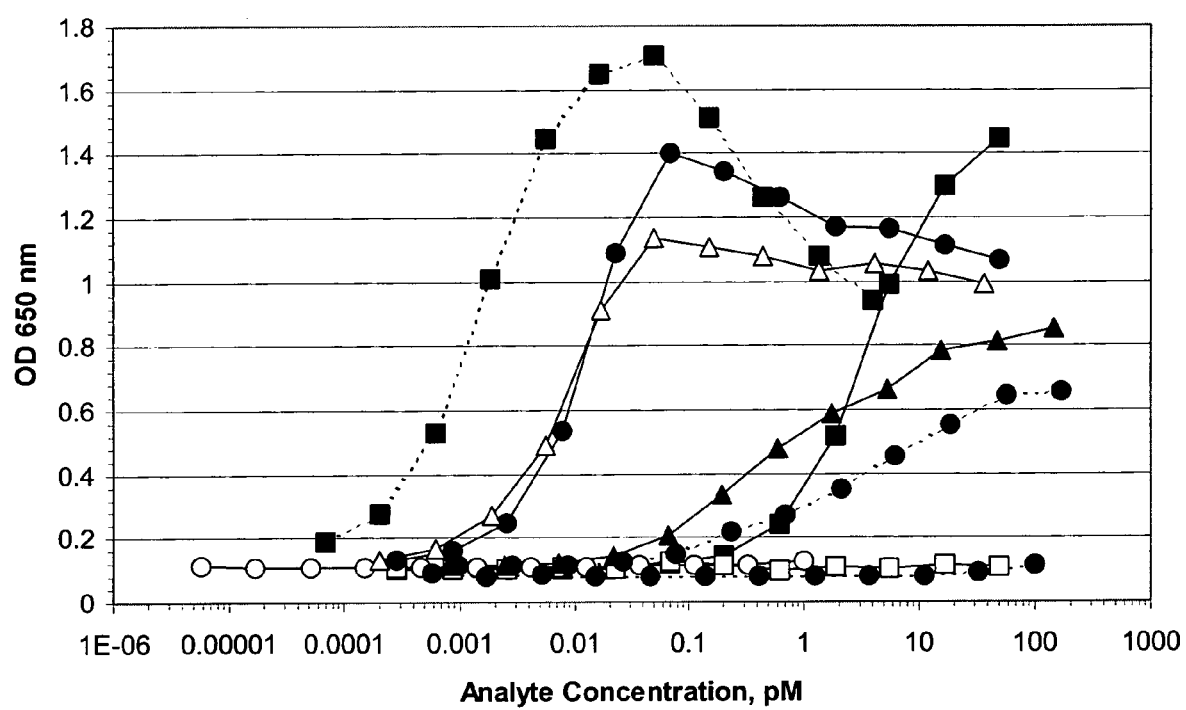
FIG. 6 is a graph depicting the results of a sandwich ELISA of MBM and various glycosaminoglycans and proteoglycans using an antibody as described herein. "OD" in the y-axis legend refers to optical density. Key to plots: aggrecan—closed square data points, dashed line; chondroitin sulfate A—closed square data points, solid line; chondroitin sulfate B—open square data points; chondroitin sulfate C—closed circle data points, solid line; hyaluronic acid—open circle data points, solid line; decorin—closed triangle data points; biglycan—open triangle data points; fibromodulin—closed circle data points, dashed line; heparan sulfate—open circle data points, dashed line.

Determination of Antibody Reactivity to Various Proteoglycans and Glycosaminoglycans Chondroitin sulfate A (bovine, C-8529), chondroitin sulfate B (porcine, C-3788), chondroitin sulfate C (piscine, C-4384), hyaluronic acid (bovine, H-7630), decorin (bovine, D-8428), biglycan (bovine, B-8041), and fibromodulin (bovine, F-6921) were purchased from Sigma. Heparan sulfate (bovine) was purchased from Calbiochem (Cat. No. 374911). Aggrecan was obtained from the source set forth in EXAMPLE 6 above. Samples were extracted using the procedures of EXAMPLE 6 and tested in the MBM sandwich ELISA with MAb 244C1 using the procedures of EXAMPLE 5, above and extracts were diluted to desired concentrations. The results from this study are presented in FIG. 6 (concentration shown in picomolar concentration (pM)). Chondroitin sulfate C showed very high reactivity in the ELISA. Chondroitin sulfate A recognition was significant but less pronounced than chondroitin sulfate C. Antibody recognition to the other glycosaminoglycans: chondroitin sulfate B (dermatan sulfate), heparan sulfate, and hyaluronic acid was negligible. While not wanting to be bound to the following statement, it is believed that the high degree of MAb 244C1 recognition for aggrecan may be due to the high chondroitin sulfate content (100 chains per molecule) of aggrecan. Biglycan, a smaller, leucine-rich proteoglycan (SLRP) containing two chondroitin sulfate or dermatan sulfate chains, showed significant reactivity whereas others in the same class, namely, decorin (one chondroitin sulfate or dermatan sulfate chain), and fibromodulin (4 keratan sulfate chains with no chondroitin sulfate) did not. While not wanting to be bound to the following statement, because MAb 244C1 recognized "free" chondroitin sulfate glycosaminoglycan it is possible that the described antibody may recognize the chondroitin sulfate moiety of aggrecan found in cartilage.

EXAMPLE 7

Identifying MBM Using an Assay for Hyaluronic Acid

Figure 7:
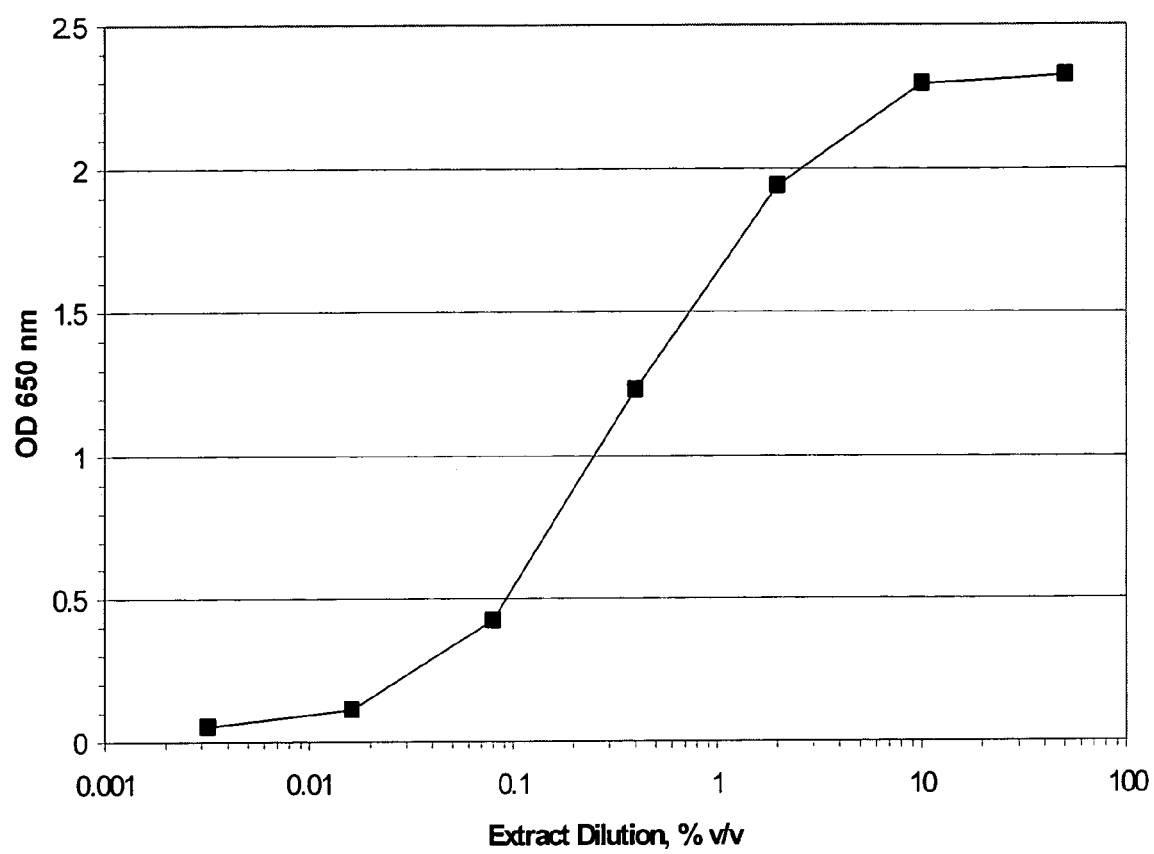
FIG. 7 is a graph depicting the results of the use of a commercially available hyaluronic acid assay to detect BMBM in varying concentrations. "OD" in the y-axis legend refers to optical density.

A hyaluronic acid test kit was obtained from Corgenix Inc., Westminster, CO. This test kit is a sandwich assay in which the ligand is bovine hyaluronic acid binding protein (HABP), which has a binding affinity for hyaluronic acid. The kit uses bound HABP on a solid phase and unbound labeled HABP to form the sandwich with hyaluronic acid. A phosphate buffered saline extract of BMBM was prepared containing 1 gram of BMBM in 10 milliliters of PBS boiled 15 minutes and then centrifuged using the centrifugation procedures of the direct bind procedures in EXAMPLE 2, above. The supernatant was then diluted to desired concentrations, and the test was conducted in accordance with the manufacturers' instructions that accompanied the test kit for various concentrations. Results are presented in FIG. 7. The hyaluronic acid standard calibration curve that accompanied the kit was used to calculate the hyaluronic acid concentration. The assay indicated that the extract had a hyaluronic acid concentration of 111.6 µg/mL, which indicated that the content in BMBM was 0.1116% (w/w).

EXAMPLE 8

Test Strip with a Two Assays

The Lateral Flow Immunochromatography Assay of EXAMPLE 3 was prepared with the following modifications. A monoclonal antibody with specificity for mammalian troponin but lacking binding affinity for avian troponin was sprayed onto a zone different from that onto which MAb 244C2 was sprayed to form a separate indicator line at a location that was visibly distinguishable from the zone onto which MAb 244C2 was sprayed. Additional monoclonal antibodies with specificity for mammalian troponin but lacking binding affinity for avian troponin are conjugated to colloidal gold and dried onto polyester pads. The pads and membranes were laminated, combined with sample filter paper and wicking paper and cut into test strips using the procedures of EXAMPLE 3 and the liquid sample is prepared, contacted, and allowed to develop according to EXAMPLE 3. The test strip was then removed from the sample and the results were interpreted. If one line is present (at the control zone), the result is negative. If a line is present only at the control zone and the zone onto which MAb 244C2 was sprayed, the result is positive for MBM, but negative for mammalian MBM. If a line is present at all three zones (the control zone and both zones onto which antibodies were sprayed) the result is positive for mammalian MBM.

EXAMPLE 9

Identifying MBM using an Immunoassay for bone protein

Figure 8:
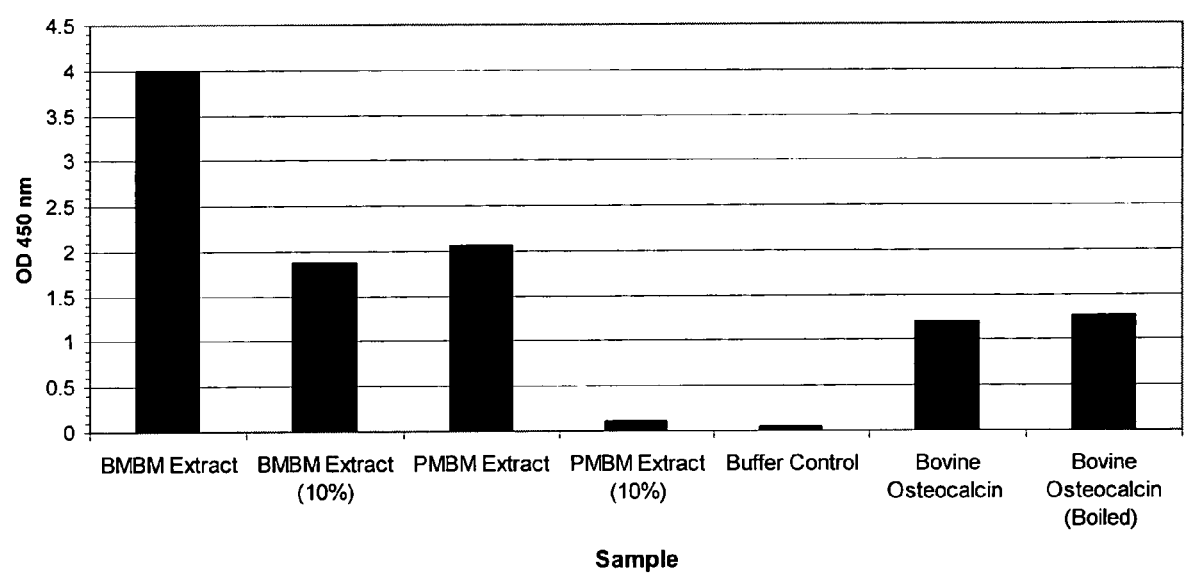
FIG. 8 is a is a bar graph depicting the results of performing a commercially-available immunoassay for osteocalcin on bovine osteocalcin and on BMBM and poultry meat and bone meal (PMBM) extracts. "OD" in the y-axis legend refers to optical density.

An osteocalcin test kit was obtained from Takara Bio Inc., Otsu, Shiga, Japan. This test kit is a two-step sandwich immunoassay that utilizes 2 monoclonal antibodies specific for the carboxylated form of osteocalcin (Gla-OC). The kit is designed for the monitoring of osteocalcin in human sera and cell cultures where it is a marker for bone disease. The kit uses one anti-bovine osteocalcin monoclonal antibody bound to the solid phase and an unbound, labeled anti-bovine osteocalcin monoclonal antibody to form a sandwich with osteocalcin. Phosphate-buffered saline extracts of bovine MBM (BMBM) or poultry MBM (PMBM) were prepared containing 1 gram of MBM in 10 milliliters of PBS. Extracts were vortexed for 15 seconds, and then centrifuged at 250×g for 10 minutes. A portion of the MBM supernatants were further diluted in PBS to 10% (v/v). Purified bovine osteocalcin was obtained from Haematologic Technologies Inc., Essex Junction, Vt. Two bovine osteocalcin solutions of 0.1 mg/mL were prepared in PBS. One aliquot (0.1 mL) of one of the solutions was boiled for 15 min. This and the non-boiled aliquot each were separately further diluted in PBS to a final concentration of 16 ng/mL. The MBM supernatants, purified bovine osteocalcin solutions (boiled and non-boiled), and a buffer control (PBS) were tested in accordance with the manufacturers' instructions that accompanied the test kit. These results are presented in FIG. 8. The osteocalcin standard calibration curve that accompanied the kit was used to calculate the osteocalcin concentration in the samples. Based on the instructions provided with the kit, the assay indicated that the BMBM extract contained 0.87 µg/mL osteocalcin whereas the PMBM extract contained 0.01 µg/mL. One possible explanation for the difference in indicated concentration is the possibility that PMBM contains less bone than BMBM. The foregoing should not be considered a binding statement, however, since other explanations are possible. For example, since the antibodies used in the kit were raised against bovine osteocalcin, the binding affinity for bovine osteocalcin may be higher for bovine osteocalcin than for avian osteocalcin resulting in a kit that is inherently more sensitive to BMBM than PMBM. Again, these possible explanations should not be considered binding. It was also shown that immunoassay reactivity was not significantly affected by boiling the osteocalcin sample for 15 min. These data demonstrate the usefulness of bone proteins as targets for the detection of rendered animal by-products such as meat and bone meal.

Although methods and materials similar or equivalent to those described herein can be used in the practice or testing of the present invention, suitable methods and material are described above. In addition, the materials, methods, and examples are illustrative only and not intended to be limiting. All publications, patent applications, patents and other cited references mentioned herein are incorporated by reference in their entirety.

The foregoing description is provided for describing various embodiments relating to the invention. Various modifications, additions and deletions may be made to these embodiments and/or structures without departing from the scope and spirit of the invention.

All patents, patent applications, and publications cited herein are incorporated by reference in their entirety. To the extent that any document incorporated by reference herein contains a definition that differs from a definition in this document, the definition in this document shall control.

What is claimed is:

1. A method for detecting rendered animal byproduct in a sample comprising:
   combining the sample suspected of containing rendered animal byproduct with a detectable antibody having binding affinity for an analyte for a time and under conditions effective to cause at least some analyte, if present, to bind which at least some antibody to form a complex;
   separating unbound antibody from the complex,
   determining existence of the complex,
   correlating the existence of the complex to determine presence of the analyte in the sample;
   wherein the antibody lacks immunoreactivity with animal muscle tissue;
   wherein the analyte is a component of rendered animal bone or connective tissue or is a component of the extracellular matrix of bone or cartilage;
   wherein the sample is animal feed or a component thereof; and
   wherein the amount of rendered animal byproduct detected by the method is about 0.005% to about 0.01% by weight.

2. The method of claim 1, wherein:
a detectable label is attached to the antibody,
combining the sample with the antibody further comprises combining the sample and antibody with a second antibody that is bound to at least one location on a solid phase for a time and under conditions effective to cause at least some analyte, if present, to bind with at least some antibody and at least some second antibody such that at least some antibody becomes immobilized in the location, and
determining the existence of the complex comprises determining whether detectable label is present in the location.

3. The method of claim 1, wherein:
a detectable label is attached to the antibody, combining the sample with the antibody further comprises combining the sample and antibody with an analyte analog that is bound to at least one location on a solid phase, wherein the antibody has a binding affinity for the analyte analog, and
determining the existence of the complex comprises determining the amount of labeled antibody present in the location.

4. The method of claim 1, wherein:
combining the sample with the antibody further comprises combining the sample and antibody with an analyte analog having a detectable label attached thereto and the antibody has a binding affinity for the analyte analog,
the antibody is bound to at least one location on a solid phase,
the method further comprises separating unbound analyte analog from bound analyte analog after the combining step and before the determining step,
determining die existence of the complex comprises determining the amount of labeled analyte analog present in the location.

5. The method of claim 1, wherein:
determining existence of the complex further comprises determining the amount of the complex, and
correlating the existence of the complex further comprises correlating the amount of complex to determine the amount of analyte present in the sample.

6. The method of claim 1, wherein the assay further comprises:
combining the sample with at least one additional antibody having binding affinity for a component of rendered animal byproduct of one or more known tax onornic groups, but having measurably lower binding affinity for rendered animal byproduct from one or more different taxonomic groups, for a time and under conditions effective to cause the second antibody to bind with the analyte, if present, to form a complex, determining existence of the second complex, and correlating the existence of the second complex to determine presence of rendered animal byproduct of a known taxonomic group or combination of taxonomic groups.

7. The method of claim 2, wherein the detectable label comprises at least one of radioactive molecules, enzymes, substrates, cofactors, inhibitors, fluorescent moieties, chemiluminescent moieties, or magnetic particles.

* * * * *